(12) United States Patent
Latour, Jr. et al.

(10) Patent No.: US 6,899,703 B2
(45) Date of Patent: May 31, 2005

(54) INTRAURETHRAL DEVICE FOR TREATING OR DETECTING VARIOUS DISEASES OR INFECTIONS OF THE URINARY SYSTEM

(75) Inventors: Robert A. Latour, Jr., Clemson, SC (US); Brent G. Carman, Fulton, KY (US)

(73) Assignee: Clemson University, Clemson, SC (US)

( * ) Notice: Subject to any disclaimer, the term of this patent is extended or adjusted under 35 U.S.C. 154(b) by 242 days.

(21) Appl. No.: 10/097,539

(22) Filed: Mar. 12, 2002

(65) Prior Publication Data

US 2002/0156458 A1 Oct. 24, 2002

Related U.S. Application Data

(60) Provisional application No. 60/275,389, filed on Mar. 13, 2001.

(51) Int. Cl.[7] ............................................... A61M 31/00
(52) U.S. Cl. .......................................... 604/517; 604/57
(58) Field of Search ..................... 600/29–32; 604/57, 604/514, 515, 517

(56) References Cited

U.S. PATENT DOCUMENTS

| | | |
|---|---|---|
| 3,117,569 A | 1/1964 | Wegner |
| 4,642,104 A | 2/1987 | Sakamoto et al. |
| 5,004,454 A | 4/1991 | Beyar et al. |
| 5,007,897 A | 4/1991 | Kalb et al. |
| 5,082,006 A | 1/1992 | Jonasson |
| 5,090,424 A | 2/1992 | Simon et al. |
| 5,114,398 A | 5/1992 | Trick et al. |
| 5,131,906 A | 7/1992 | Chen |
| 5,140,999 A | 8/1992 | Ardito |
| 5,306,226 A | 4/1994 | Salama |
| 5,476,434 A | 12/1995 | Kalb et al. |
| 5,479,945 A * | 1/1996 | Simon ........................ 128/885 |
| 5,554,147 A | 9/1996 | Batich et al. |
| 5,607,417 A | 3/1997 | Batich et al. |
| 5,624,395 A | 4/1997 | Mikhail et al. |
| 5,670,111 A | 9/1997 | Conway et al. |
| 5,671,755 A | 9/1997 | Simon et al. |
| 5,724,994 A | 3/1998 | Simon et al. |
| 5,749,826 A | 5/1998 | Faulkner |
| 5,788,687 A | 8/1998 | Batich et al. |
| 5,806,527 A | 9/1998 | Borodulin et al. |
| 5,813,974 A | 9/1998 | Doladé Guardia |
| 5,887,593 A | 3/1999 | Levius |
| 5,906,575 A | 5/1999 | Conway et al. |
| 5,910,316 A | 6/1999 | Keefer et al. |

(Continued)

FOREIGN PATENT DOCUMENTS

| | | |
|---|---|---|
| WO | WO 02071922 | 9/2002 |
| WO | WO 02071978 | 9/2002 |

OTHER PUBLICATIONS

U.S. Appl. No. 09/805,581, filed Mar. 13, 2001, Robert A. Latour, Jr., "Intraurethal Device for Incontinence."
Thesis entitled "Design Of An Intra–Urethral Device For Incontinence" prepared by Elizabeth M. Burke (Dec., 1996).
PCT Search Report, Dec. 3, 2002.

*Primary Examiner*—Michael J. Hayes
(74) *Attorney, Agent, or Firm*—Dority & Manning, P.A.

(57) ABSTRACT

An intraurethral device for use in a female urinary tract is provided. The intraurethral device comprises a urethral element that contains a chemical compound capable of treating or detecting the presence or absence of a disorder or disease. In one embodiment, the intraurethral device also contains outer and inner insertion elements that are in operative communication with the urethral element to facilitate the insertion of the urethral element into the urethra without substantially contaminating the chemical compound prior to insertion.

8 Claims, 6 Drawing Sheets

U.S. PATENT DOCUMENTS

| | | |
|---|---|---|
| 5,916,176 A | 6/1999 | Caillouette |
| 5,954,688 A * | 9/1999 | Adams et al. ................ 604/59 |
| 5,954,869 A | 9/1999 | Elfersy et al. |
| 5,959,014 A | 9/1999 | Liebeskind et al. |
| 5,989,179 A * | 11/1999 | Migachyov .................. 600/29 |
| 6,039,967 A | 3/2000 | Ottoboni et al. |
| 6,070,588 A | 6/2000 | Pham |
| 6,090,038 A | 7/2000 | Zunker et al. |
| 6,090,098 A | 7/2000 | Zunker et al. |
| 6,142,928 A | 11/2000 | Zunker et al. |
| 6,171,230 B1 | 1/2001 | Hakky et al. |
| 6,440,060 B1 | 8/2002 | Latour, Jr. |
| 2003/0050612 A1 * | 3/2003 | Mulholland et al. ........ 604/278 |

* cited by examiner

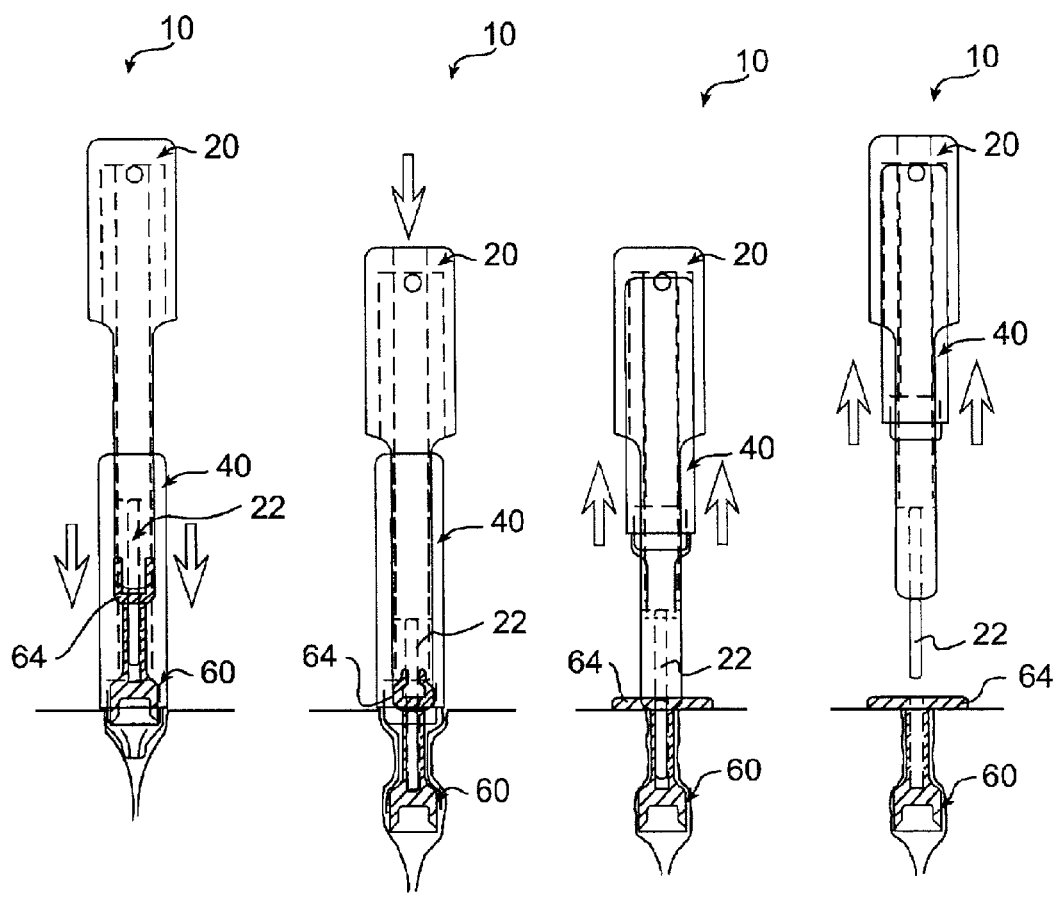
FIG. 2A  FIG. 2C
FIG. 2B  FIG. 2D

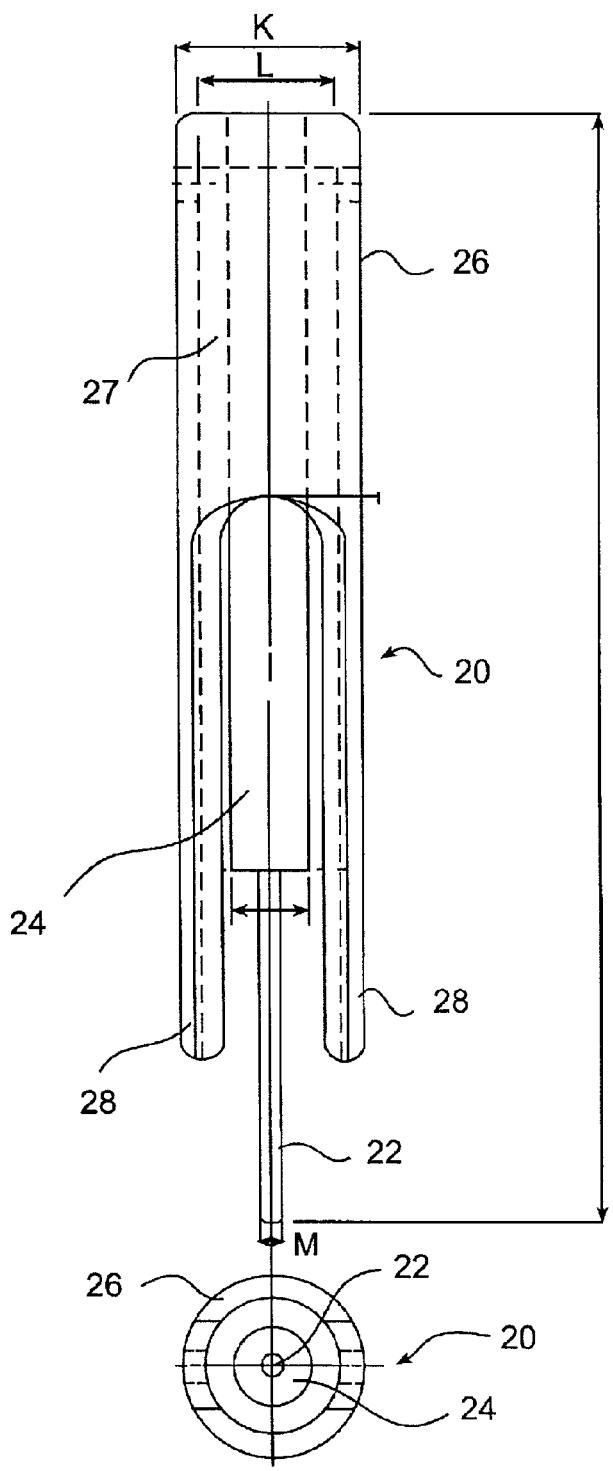
FIG. 3A
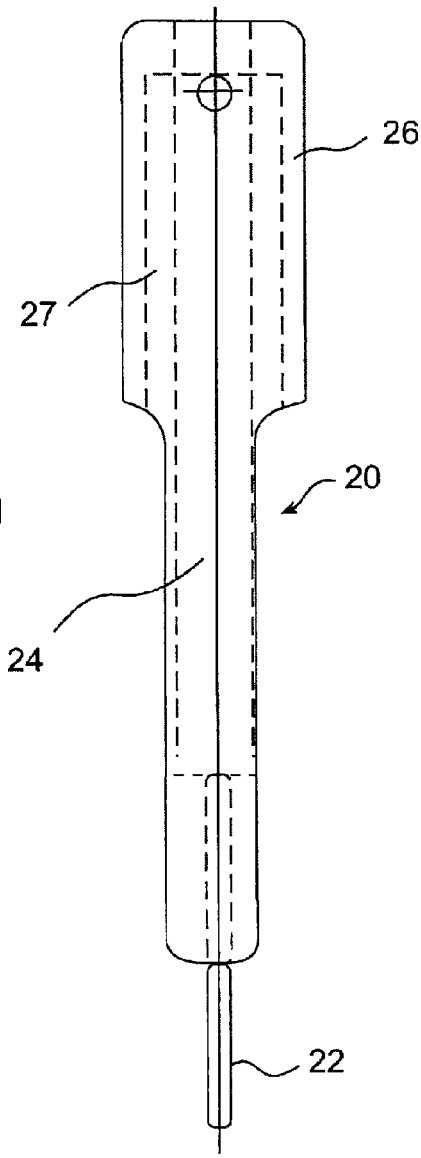
FIG. 3B
FIG. 3C

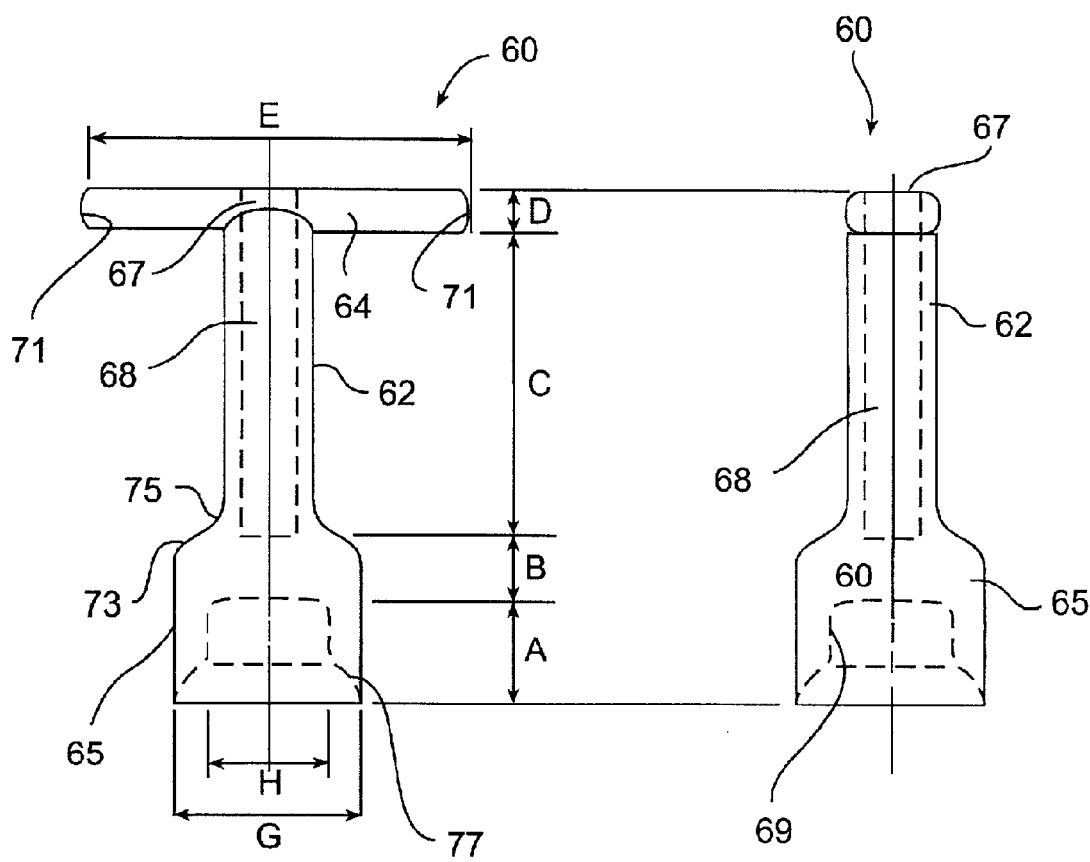
FIG. 6A  FIG. 6B
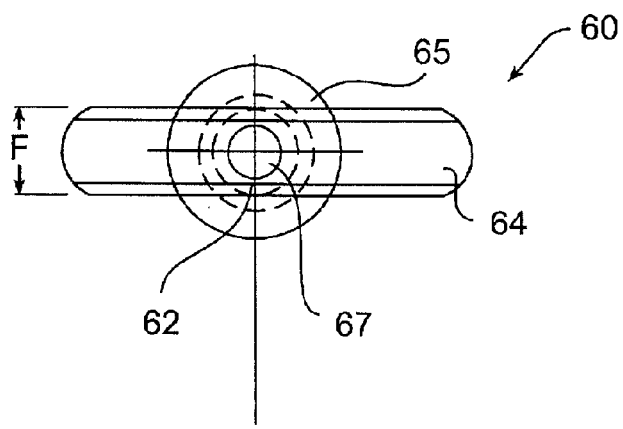
FIG. 6C ly, such a laboratory analysis may require
INTRAURETHRAL DEVICE FOR TREATING OR DETECTING VARIOUS DISEASES OR INFECTIONS OF THE URINARY SYSTEM

RELATED APPLICATIONS

The present application claims priority to a provisional application filed on Mar. 13, 2001 having Ser. No. 60/275,389.

BACKGROUND OF THE INVENTION

When treating or detecting various disorders or diseases in females (humans or animals), it is often desired to place a certain material in communication with the urinary system (e.g., urinary tract, bladder, kidneys, etc.) via the urethra. For example, many common conditions of the bladder or urinary tract, such as cancer, inflammation, infection or incontinence, may be treated by pharmaceutically active compounds. In the past, these compounds were orally administered.

However, one problem with oral administration is that local administration (e.g., directly into the urinary system) is typically more effective in treating many urinary disorders. As a result, drugs have also been directly injected into the desired location, such as directly injecting a drug into the bladder. Nevertheless, one problem with this approach, is that for chronic conditions, such as incontinence, the patient must be repeatedly catheterized, thus requiring frequent attention by trained medical staff. The potential for infection is also increased by repeated catheterization into the bladder. Thus, a need currently exists for an improved method of treating various infections and diseases of the urinary system.

Moreover, besides being treated through the urethra, it is often desired that certain disorders and diseases of the urinary system also be detected through the urethra as well. For instance, conventional detection mechanisms for bladder or kidney disease typically involve a detailed urine analysis. Specifically, a patient is initially asked to provide a urine specimen. This specimen is then taken to a lab and analyzed in detail by a lab technician or medical professional. Unfortunately, such a laboratory analysis may require a substantial amount of time and be relatively expensive. Moreover, because the urine sample is exposed to the environment, it can potentially become contaminated prior to testing, thereby adversely affecting the overall test results. Accordingly, a need also currently exists for an improved method of detecting various diseases and infections of the urinary system.

SUMMARY OF THE INVENTION

In accordance with one embodiment of the present invention, an intraurethral device is disclosed for use in a female urinary tract to treat or detect the presence or absence of a disorder or disease. The intraurethral device comprises a urethral element having a distal end and a proximal end. In one embodiment, the shape of the distal end forms a generally concave surface that enables the urethral element to form a seal with the urethra when inserted therein. Such a seal can inhibit urinary leakage during detection and/or treatment.

In addition, the distal end of the urethral element is adapted to be inserted into a urethra and also contains a chemical compound capable of treating or detecting the presence or absence of a disorder or disease. The chemical compound can generally vary depending on the type of disease or disorder, and whether it is desired to treat or detect such a disease or disorder. For example, doxorubicin can be used to treat various bladder infections. Moreover, a *mycobacterium*, such as *Bacillus* Calmette-Guerin, can also be utilized for treatment of carcinoma located in the bladder. In addition, other chemical compounds that can be utilized for disease and/or disorder treatment include, but are not limited to, antibiotics, such as Amoxicillin ("Amoxil") or trimethoprimsulfamethoxazole ("Bactrim DS"); hormones, such as estrogen; anesthetic lidocaine; astringents, such as silver nitrate; anti-inflammatory agents, such as dimethyl sulfoxide ("DMSO"); medications, such as indomethacin ("Indocin"); sodium pentosan-polysulfate ("Elmiron"); oxychorosens ("Clorpactin"), natruim chromogulcate; steroids, such as prendisonlone; quinolones, such as "Cipro" and "Levaquin"; and the like.

The intraurethral device also contains a first insertion element and a second insertion element. The first insertion element has an inner surface and an outer surface, wherein at least a portion of the first insertion element is operative communication with the urethral element. The second insertion element has an inner surface and an outer surface, wherein the second insertion element defines a channel through which the proximal end of the urethral element is capable of being inserted. The inner surface of the second insertion element is placed adjacent to the outer surface of the first insertion element such that the second insertion element is in operative communication with the first insertion element. The first and second insertion elements are configured to insert the urethral element into the urethra.

To further prevent contamination of the chemical compound, the intraurethral device can also contain an enclosure that surrounds at least a portion of the urethral element. In one embodiment, for example, the enclosure comprises a roll-out nipple.

In accordance with another embodiment of the present invention, a method is disclosed for treating a disease or disorder. The method comprises: a) providing an intraurethral device that comprises a urethral element having a distal end and a proximal end, the distal end of the urethral element being adapted to be inserted into a urethra, the distal end containing a chemical compound capable of treating or detecting the presence or absence of a disorder or disease; b) inserting said urethral element into the urethra so that the chemical compound is not substantially contaminated prior to insertion of the urethral element in the urethra; and c) allowing the chemical compound to be released from the urethral element into the urethra.

In accordance with still another embodiment of the present invention, a method is disclosed for detecting the presence or absence of a disease or disorder. The method comprises a) providing an intraurethral device that comprises a urethral element having a distal end and a proximal end, the distal end of the urethral element being adapted to be inserted into a urethra, the distal end containing a chemical compound capable of treating or detecting the presence or absence of a disorder or disease; b) inserting the urethral element into the urethra so that the chemical compound is not substantially contaminated prior to insertion of the urethral element in the urethra; c) allowing the chemical compound to be released from the urethral element into the urethra; d) removing the urethral element from the urethra, and e) evaluation the chemical compound to determine whether a disease or disorder is present.

Other features and aspects of the present invention are described in more detail below.

BRIEF DESCRIPTION OF THE DRAWINGS

FIG. 2 illustrates one embodiment of the present invention, in which FIG. 2A shows the alignment of the intraurethral device with a urethra, FIG. 2B shows the initial insertion of the urethral element into the urethra, FIG. 2C shows the partial withdrawal of the outer insertion element of the urethral element, and FIG. 2D shows the complete withdrawal of both of the insertion elements;

FIG. 3 illustrates the outer insertion element of one embodiment of an intraurethral device of the present invention, in which FIG. 3A is a front view of the outer insertion element, FIG. 3B is a side view of the outer insertion element; and FIG. 3C is a bottom view of the outer insertion element;

FIG. 4 illustrates the inner insertion element of one embodiment of an intraurethral device of the present invention, in which

FIG. 5 illustrates one embodiment of an intraurethral device of the present invention, in which FIG. 6 illustrates the urethral element of one embodiment of an intraurethral device of the present invention, in which FIG. 6A is a front view of the urethral element, FIG. 6B is a side view of the urethral element; and FIG. 6C is a top view of the urethral element.

Figure 1:
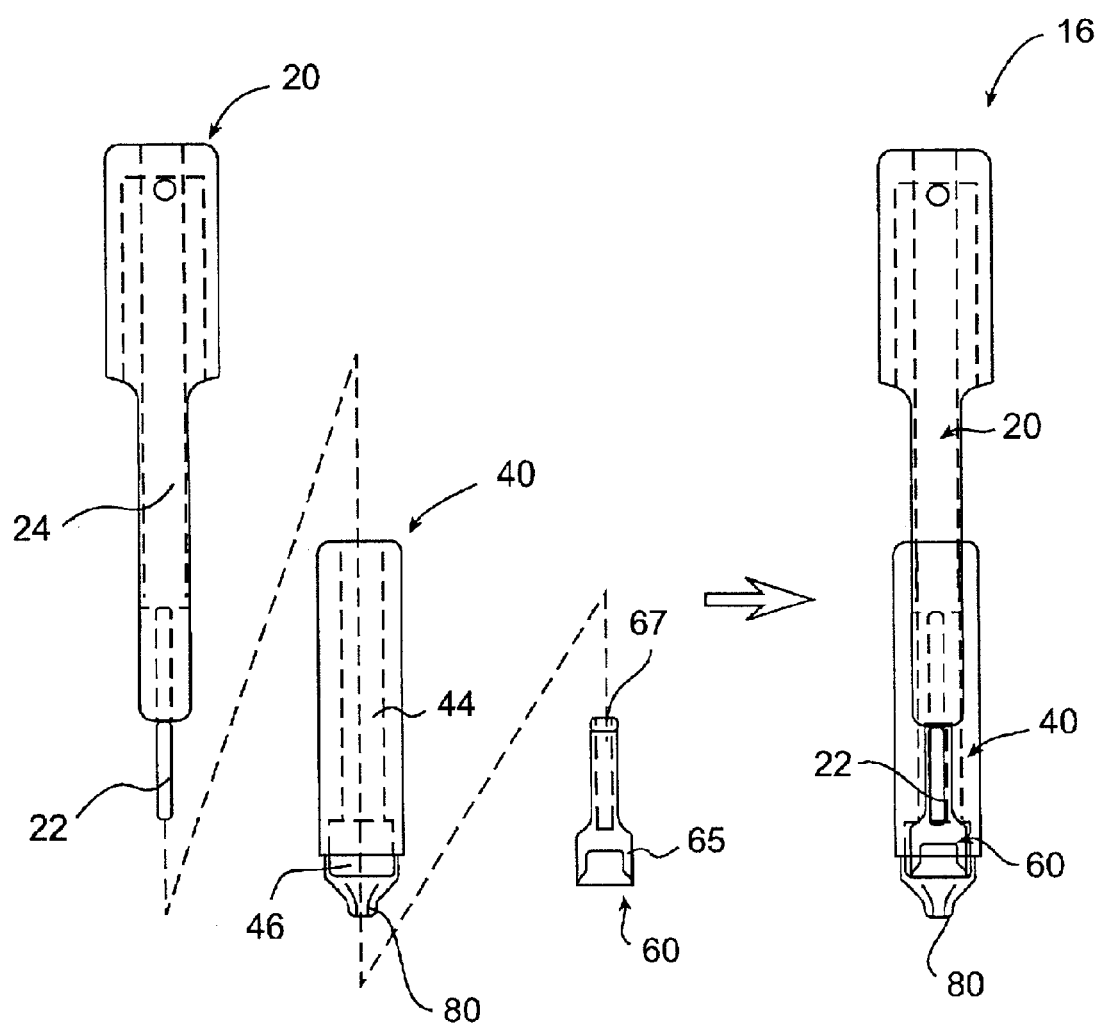
FIG. 1 illustrates one embodiment of an intraurethral device of the present invention.

Repeat use of reference characters in the present specification and drawings are intended to represent same or analogous features or elements.

DETAILED DESCRIPTION OF THE REPRESENTATIVE EMBODIMENTS

It is to be understood by one of ordinary skill in the art that the present discussion is a description of exemplary embodiments only, and is not intended as limiting the broader aspects of the present invention, which broader aspects are embodied in the exemplary construction.

The present invention is generally directed to an intraurethral device that can be used to detect and/or treat various diseases or disorders of the urinary system (e.g., urinary tract, bladder, kidneys, etc.). Specifically, an intraurethral device of the present invention can be easily inserted into a urethra in a clean and/or sterile manner. In one embodiment, the intraurethral device can deliver one or more chemical compounds to the urethra for treating one or more diseases or disorders of the urinary system. In another embodiment, the intraurethral device can contain one or more indicator materials that are designed to quickly signal the presence or absence of a certain disease or disorder in the urinary system.

In accordance with the present invention, regardless of whether utilized for treatment or detection, a urethral element is typically utilized that can be removably inserted into a urethra. In general, any device known in the art that can be inserted into a urethra can be utilized in the present invention. For example, urethral plugs inserted into the urethra to physically inhibit urinary leakage can be used in the present invention.

Referring to FIGS. 6A–6C, for instance, one embodiment of a urethral element that can be utilized in the present invention will now be described in more detail. In this embodiment, a urethral element 60 is shown that includes a distal end 65 connected to a proximal end 64 by a tubular section 62. Specifically, the proximal end 64 is an external flange that is capable of substantially preventing over-insertion of the urethral element 60 and/or to aid in the removal of the urethral element 60. Moreover, the distal end 65 has a cup-shape that forms a generally concave surface 69. It should be understood, however, that the present invention is not limited to a cup-shaped urethral element and that any other shape capable of providing a generally concave surface can also be utilized. Further, it should also be understood that a generally concave surface is not required in all embodiments of the present invention.

In general, the urethral element 60 can be made in a variety of ways. Typically, the urethral element 60 can be made from a material that is generally biocompatible such that it is suitable for contact with the urethra. In some embodiments, the urethral element 60 can be made from a biocompatible material that is also flexible. Although not required, flexible materials can sometimes allow the urethral element 60 to form a better seal with the walls of the urethra. For instance, some examples of suitable flexible materials can include, but are not limited to, elastomeric polymers, such as polyurethane, silicone rubber, natural rubber, polyester, chloroprene, polybutadiene, combinations thereof, or any other elastomeric material suitable for urethral and urine contact. One particular example of an elastomer suitable for use in making the urethral element 60 is silicone rubber, such as medical grade silicone rubber commonly used in various medical devices. However, it should be understood that any other elastomeric material can be used in the present invention.

Moreover, the urethral element 60 need not be made from the same material(s). For example, the cup-shaped end 65, the tubular section 62, and the external flange 64 may all contain different material(s), if desired. In one embodiment, for instance, the cup-shaped end 65 can be made from a flexible elastomeric material, while the external flange 64 and the tubular section 62 can conversely be made from a less flexible or non-flexible material.

The component(s) of the urethral element 60 can also generally possess any desired dimension or shape. In general, a physician usually determines the precise size for use, after measuring the patient's urethra. In particular, a urethral element 60 can be made into a variety of different shapes and sizes to better conform to different urethras. Moreover, in some embodiments, because the urethral element 60 can also conform to the size and shape of the urethra after insertion, there may be no need to custom make the urethral element.

For example, in one embodiment, as shown in FIGS. 6A–6B, the urethral element 60 can have a total length of between about 15 millimeters ("mm") to about 30 mm in length, and in one particular embodiment, the length can be about 25 mm. In particular, as shown, the total length of the urethral element 60 is approximately equal to the combined values of the dimensions represented as "a", "b", "c", and "d". These dimensions can generally be selected to have any value, depending on the desired shape and size of the urethral element. For example, in one embodiment, the dimensions represented as "a", "b", "c", and "d" are 5.0 mm, 3.0 mm, 15 mm, and 2 mm, respectively.

Besides having a certain length, the component(s) of the urethral element 60 can also have other varying dimensions. For example, in some embodiments, the outer diameter of the tubular section 62 can be between about 2 mm to about 8 mm, and in one particular embodiment, about 4.0 mm. Further, in some instances, the tubular section 62 can define a hollow channel 68 that extends through the flange 64 to form a urethral element opening 67. Thus, in this embodiment, the inner diameter of the tubular section 62 can be between about 1 mm to about 7 mm, and in one particular embodiment, about 2.5 mm.

In addition, the width dimension "e" of the flange 64 can be between about 10 mm to about 40 mm, and in one particular embodiment, about 18 mm. Moreover, the thickness dimension "f" of the flange 64 can be between about 2 mm to about 8 mm, and in one particular embodiment, about 4.0 mm. The outer edges 71 of the flange 64 can also be rounded, such as having a radius of curvature of about 2.0 mm.

Further, the cup-shaped end 65 can also possess a variety of different dimensions. For example, in the illustrated embodiment, the cup-shaped end 65 has an outer diameter "g" of between about 4 mm to about 16 mm, and in one particular embodiment, about 8.0 mm. Moreover, the cup-shaped end 65 also has an inner diameter "h" of between about 3 mm to about 15 mm, and in one particular embodiment, about 5.0 mm. In addition, as shown, the cup-shaped end 65 can contain one or more rounded surfaces. For example, in one embodiment, as shown in FIG. 6A, the cup-shaped end 65 contains a rounded surface 77, which has a radius of curvature of about 5.0 mm. Moreover, as shown, the urethral element 60 can also contain rounded surfaces 73 and 75, which have a radius of curvature of about 2.5 mm and about 4.0 mm, respectively. In one embodiment, these rounded surfaces can minimize tissue irritation within the urethra.

In general, a variety of chemical compounds can be applied to the urethral element 60 for treatment of various diseases and disorders. For example, doxorubicin can be used to treat various bladder infections. Moreover, a *mycobacterium*, such as *Bacillus* Calmette-Guerin, can also be utilized for treatment of carcinoma located in the bladder. In addition, other chemical compounds that can be utilized for disease and/or disorder treatment include, but are not limited to, antibiotics, such as Amoxicillin ("Amoxil") or trimethoprimsulfamethoxazole ("Bactrim DS"); hormones, such as estrogen; anesthetic lidocaine; astringents, such as silver nitrate; anti-inflammatory agents, such as dimethyl sulfoxide ("DMSO"); medications, such as indomethacin ("Indocin"); sodium pentosan-polysulfate ("Elmiron"); oxychorosens ("Clorpactin"), natruim chromogulcate; steroids, such as prendisonlone; quinolones, such as "Cipro" and "Levaquin"; and the like.

In addition, other useful chemical compounds that can be used for treatment of various diseases and disorders of the urinary system may be described in U.S. Pat. No. 4,642,104 to Sakamoto, et al.; U.S. Pat. No. 5,007,897 to Kalb, et al.; U.S. Pat. No. 5,479,945 to Simon; U.S. Pat. No. 5,554,147 to Batich, et al.; U.S. Pat. No. 5,607,417 to Batich, et al.; 5,749,826 to Faulkner; 5,788,687 to Batich, et al.; and U.S. Pat. No. 6,039,967 to Ottoboni, et al., which are incorporated herein in their entirety by reference thereto for all purposes.

Figure 5A:
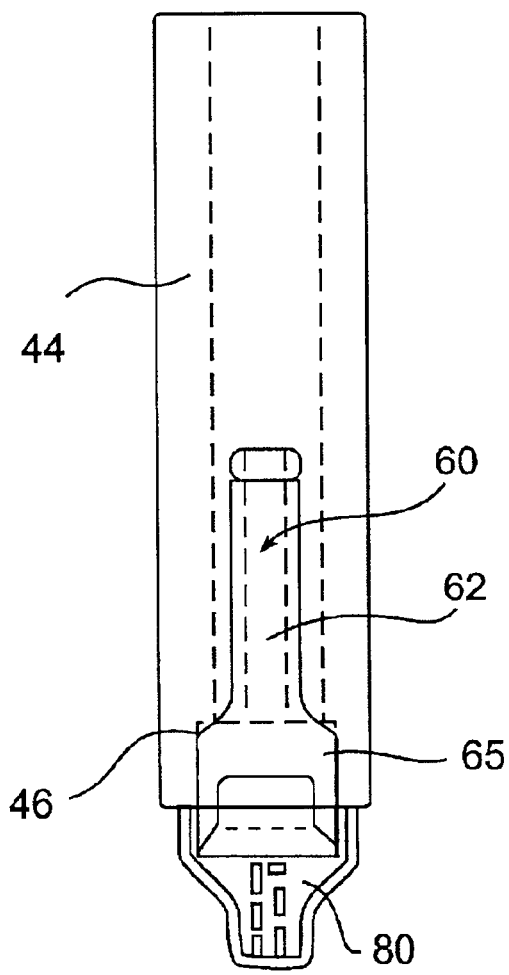
FIG. 5A shows a roll-out nipple in its rolled-up position and FIG. 5B shows the roll-out nipple in its unraveled position.
Figure 5B:
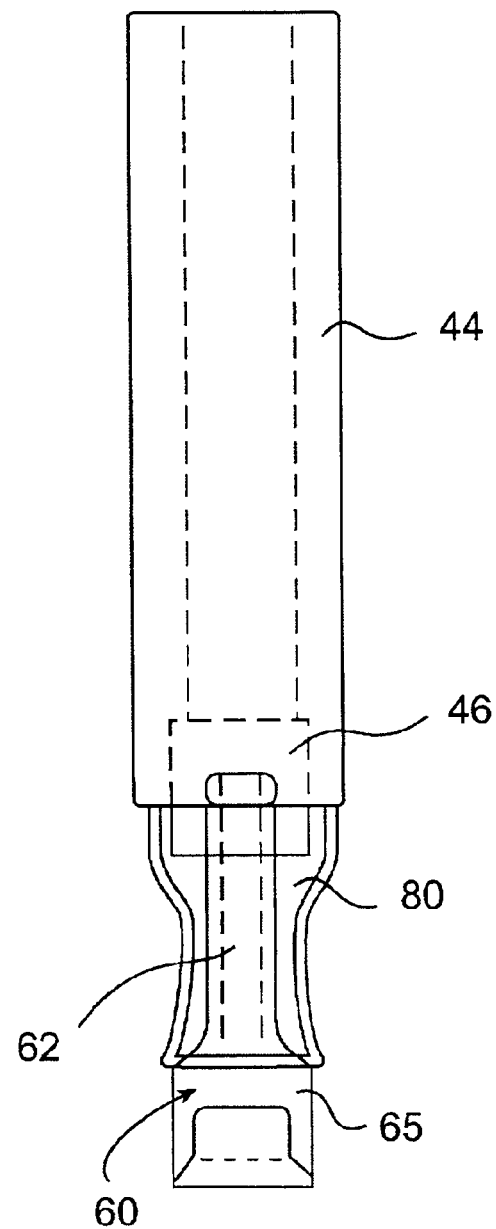

When utilized, a chemical compound for treating various diseases and disorders, such as described above, can be applied to the urethral element 60 in a variety of ways. For instance, in some embodiments, the compound(s) can be contained within the cavity formed by the cup-shaped end 65 of the urethral element 60. In some embodiments, as shown in FIGS. 5A–5B, an enclosure, such as a roll-out nipple 80, can be utilized to cover the urethral element 60 prior to its insertion into the urethra. The nipple 80 can ensure that the compound(s) are only applied upon insertion into the urethra and that the urethral element 60 is applied in a relatively clean and/or sterile manner. The nipple 80 can be made from any of a variety of materials, such as various plastics or rubber materials. If desired, certain adhesives (e.g., starch) may also be utilized to ensure that the nipple 80 remains enclosed at its tip prior to use of the intraurethral device.

Besides being contained within the cavity formed by the urethral element 60, the treatment compounds can be also be applied to the urethral element 60 in various other ways. For instance, in some embodiments, the chemical compound(s) can be coated onto the outer surface of the urethral element 60, such as to the outer surface of the cup-shaped end 65 or the tubular section 62. In other embodiments, the chemical compound(s) can be incorporated into the polymer used to form the urethral element 60. In particular, when incorporated into the polymer, the chemical compound can be configured to controllably release from the urethral element 60 as it remains within the urethra. It should be understood that the present invention is not limited to any particular method or device for applying the chemical treatment compound(s) to the urethra, and that other methods and devices are also contemplated by the present invention.

As mentioned above, besides being capable of treating various diseases and disorders of the urinary system, the intraurethral device of the present invention is also capable of detecting the presence of such diseases and disorders. For instance, in one embodiment, an indicator strip (not shown) can be disposed around the inner surface of the cup-shaped end 65 of the urethral element 60. It should be understood, however, that the indicator strip may be disposed on any portion of the urethral element 60, so long as the materials on the strip are capable of being placed into communication with the bodily fluids of the patient.

The indicator strip may contain one or a plurality of indicator materials that are well known in the art for detecting such urinary diseases or disorders. For example, in some instances, the indicator material(s) can turn one color upon the detection of a certain chemical, and remain the same, or turn another color, in the absence of the chemical. Furthermore, the indicator material(s) may also detect the severity of a problem, such as by turning a darker color if the detected disorder or disease is more severe.

For example, if desired, the indicator strip can contain one or more known materials that are capable of detecting certain chemicals, such as ketones, proteins, red blood cells, white blood cells, glucose, nitrates, hemoccult, calcium, oxalates, blood urea nitrogen, and the like. When detected, these chemicals, among others, can provide a clinical sign to a medical professional or user of a variety of possible disorders and diseases. In addition, the indicator strip can also contain other indicator materials as well, such as a material capable of measuring pH.

To utilize the intraurethral device of the present invention to detect the presence or absence of a certain disease or disorder, the urethral element 60 is first inserted into a urethra so that the indicator materials(s) can be placed into communication with urine and other fluids within the urethra. If a selected disease or disorder is present (or absent), the indicator(s) may then react (e.g., change color) to indicate the presence of such disease or disorder. As such, when the urethral element 60 is withdrawn, a user or medical professional can easily determine whether such disease or infection is present within the patient's urinary system.

Besides utilizing an indicator strip, it should be understood that indicator material(s) may also be directly applied to the urethral element 60, if desired. In fact, any other method for detecting the presence of various diseases and disorders can be utilized in conjunction with the intraurethral device of the present invention.

In general, the urethral element 60, which contains various materials for disease treatment and/or detection, can be inserted into a urethra in a variety of ways. For example, in one embodiment, a user or medical professional may directly and manually insert the urethral element 60 into the urethra. In other embodiments, the urethral element 60 can be inserted into the urethra with the assistance of one or more insertion devices. Such insertion devices can inhibit contamination of the chemical compound of the urethral element 60 prior to insertion into the urethra. Moreover, insertion devices can also facilitate self-insertion of the urethral element 60 by a user.

Referring to FIGS. 1, 3A–3C, and 4A–4C, for example, one embodiment of an intraurethral device 10 that utilizes a urethral element 60 in conjunction with an outer insertion element 20 and an inner insertion element 40 is illustrated. As shown in FIGS. 3A–3C, the outer insertion element contains an inner body portion 24 that is attached at one end to an outer body portion 26. In addition, the outer insertion element 20 also contains an elongated element 22 (e.g., shaft) that is attached at one end to the inner body portion 24. In general, any of a variety of attachment mechanisms, such as adhesives, can be utilized in attaching the portions of the outer insertion element 20. Moreover, instead of being formed from multiple portions, the outer insertion element 20 can also be formed as one integral portion.

The portion(s) of the outer insertion element 20 can be formed to have a variety of different shapes and/or sizes. For example, in one embodiment, as shown in FIGS. 3A–3C, the elongated element 22, the inner body portion 24, and the outer body portion 26 have a cylindrical, tube-like shape. These portions may be solid or define a hollow channel. For example, in the illustrated embodiment, the outer body portion 26 defines a cylindrical, tube-like channel 27 for placement of the inner body portion 24 therein.

When having a cylindrical shape, the diameter of the elongated element 22, the inner body portion 24, and the outer body portion 26 can generally vary. For instance, in one embodiment, the outer diameter "i" of the inner body portion 24 can be about 6.9 mm, the outer diameter "k" of the outer body portion 26 can be about 16.0 mm, the inner diameter "l" of the outer body portion 26 can be about 12.1 mm, and the outer diameter "m" of the shaft 22 can be about 2.0 mm.

Besides having a certain diameter (or width), the length of one or more portions of the outer insertion element 20 can also be selectively varied as desired. In one embodiment, for instance, the length "n" of the entire insertion element 20 can be about 100 mm. Specifically, in the illustrated embodiment, the length of the elongated element 22 is about 32 mm and the length of the inner body portion 24 is about 68 mm. Further, in one embodiment, the length of the outer body portion 26 (including the flanges 28) can be about 86.0 mm and the length of the hollow channel 27 defined by the outer body portion 26 can be about 35.0 mm.

In accordance with one embodiment of the intraurethral device of the present invention, an additional inner insertion element 40 is utilized in operative communication with the outer insertion element 20 to facilitate insertion of the urethral element 60 into a urethra. Moreover, the inner insertion element 40 can also help to maintain the sterility and/or cleanliness of the urethral element 60 prior to its insertion into a urethra.

Figures 4A, 4B, 4C:
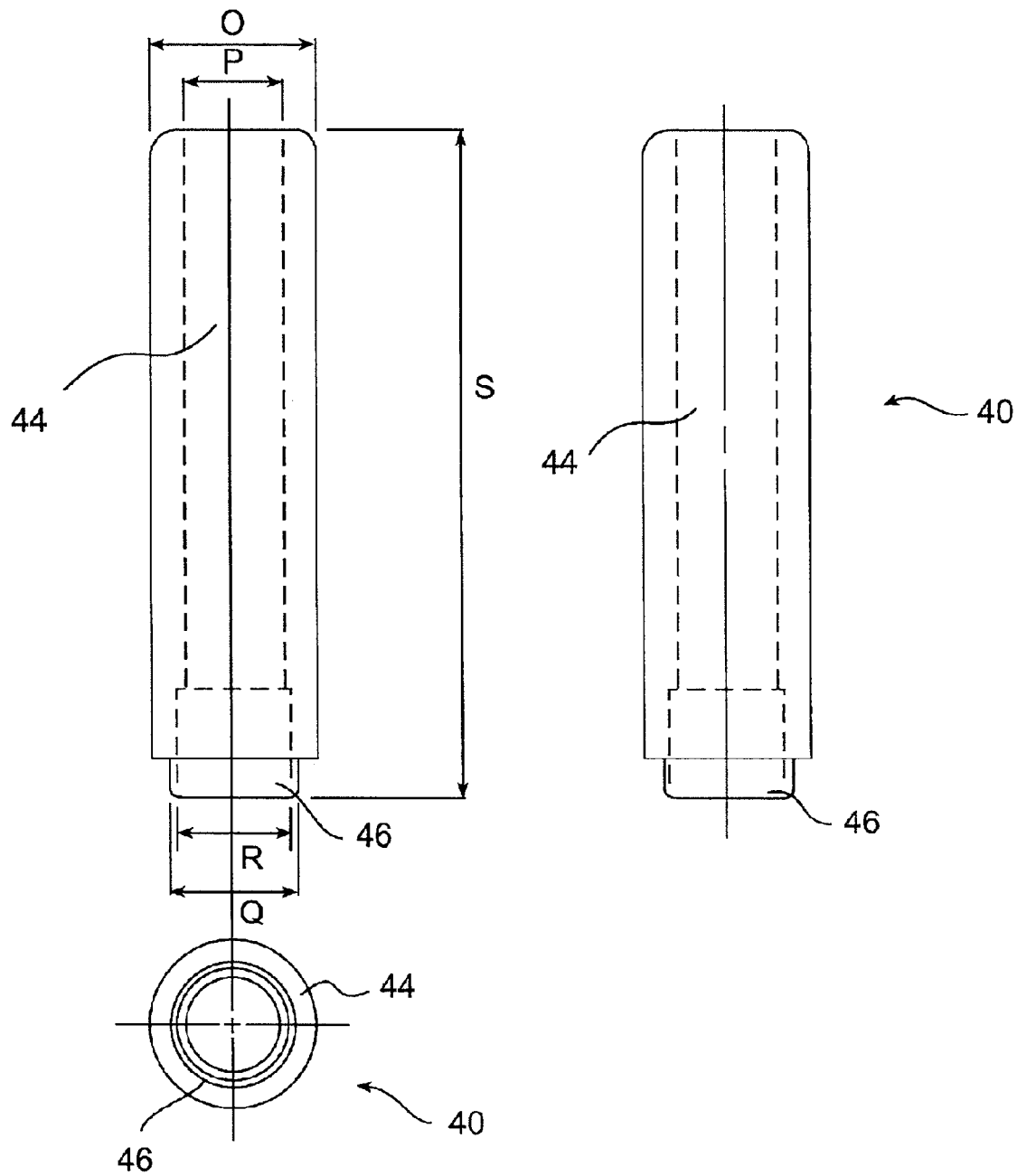
FIG. 4A is a front view of the inner insertion element.
FIG. 4B is a side view of the inner insertion element.
FIG. 4C is a bottom view of the inner insertion element.

For example, referring to FIGS. 4A–4C, one embodiment of an inner insertion element 40 that can be used in the present invention is illustrated. As shown, the inner insertion element 40 contains a first body portion 44 attached to a second body portion 46. Specifically, in this embodiment, the outer cylindrical surface of the second body portion 46 is attached to the inner cylindrical surface of the first body portion 46. In general, any of a variety of attachment mechanisms (e.g., adhesives, etc.) can be utilized to attach the portions 44 and 46 of the inner insertion element 40. Moreover, instead of being formed from multiple portions, the inner insertion element 40 can also be formed as one integral portion.

The portion(s) of the inner insertion element 40 can generally be formed to have a variety of different shapes and/or sizes. For example, in one embodiment, as shown in FIGS. 4A–4C, the first body portion 44 and the second body portion 46 have a cylindrical, tube-like shape. Moreover, in the illustrated embodiment, both the first and second body portions 44 and 46 define cylindrical, tube-like channels for placement of the inner insertion element 20 therein, as will be described in more detail below.

When having a cylindrical shape, the diameter of the first body portion 44 and the second body portion 46 can generally vary. In one embodiment, for instance, the outer diameter "o" of the first body portion 44 can be about 12.0 mm, the inner diameter "p" of the first body portion 44 can be about 7.0 mm, the outer diameter "q" of the second body portion 46 can be about 9.1 mm, and the inner diameter "r" of the second body portion 46 can be about 8.1 mm.

Besides having a certain diameter (or width), the length of one or more portions of the inner insertion element 40 can also be selectively varied as desired. In one embodiment, for instance, the length "s" of the entire insertion element 40 can be about 50 mm. In particular, in the illustrated embodiment, the length of the first body portion 44 is about 47 mm, the length of the second body portion 46 is about 8 mm, and the portion 46 extends beyond the portion 44 by approximately 3 mm.

In general, the portion(s) of the insertion elements 20 and 40 can be made any of a variety of materials, such as rigid and/or semi-rigid materials. In some embodiments, for instance, the insertion elements 20 and 40 can contain plastic materials, such as polyolefins, polyamides, polycarbonates, etc; paper materials, such as cardboard; and the like. Moreover, in another embodiment, the insertion elements 20 and 40 can contain a semi-rigid rubber material, such as polyurethane. It should be understood, however, that the insertion elements 20 and 40 need not be made from the same material. Moreover, the components of a single insertion element can also be made from different materials if desired.

As mentioned above, in some embodiments, a nipple 80 can be utilized to at least partially enclose the urethral element 60 prior to its insertion into the urethra. For instance, as shown in FIGS. 5A–5B, in one embodiment, the nipple 80 can be attached to the second body portion 46 of the inner insertion element 40 in such a manner that the nipple 80 substantially covers the urethral element 60 prior to its insertion in a urethra. The nipple 80 can be sealed to the inner insertion element 40 according to any sealing method known in the art. If desired, still other devices can be utilized to enhance the ability of the urethral element 60 to remain relatively sterile and/or clean prior to and/or during insertion. For example, in one embodiment, some or all of the intraurethral device 10 can be enclosed with an additional sterile bag (not shown).

In one embodiment, the components described above can be assembled to form the intraurethral device according to the process illustrated in FIG. 1. Such assembly can be performed by a user, a medical professional, or during manufacture of the device. For instance, referring to FIG. 1, the inner insertion element 40 can initially be placed into operative communication with the outer insertion element 20 by positioning the inner cylindrical surface of the first body portion 44 over the outer cylindrical surface of the inner body portion 24 such that the inner insertion element 40 fits between the flanges 28 of the outer insertion element 20. (See FIGS. 3A–3C). As a result, the inner insertion element 40 can slide along the entire length of the inner body portion 24.

Thereafter, the inner insertion element 40 is moved along the length of the inner body portion 24 of the outer insertion element 20 such that at least a portion of the elongated element 22 extends beyond the inner insertion element 40. Once positioned in this manner, the urethral element opening 67 of the urethral element 60 is then placed over the portion of the elongated element 22 that extends beyond the inner insertion element 40. However, it should be understood that the urethral element 60 can generally be connected to the elongated element 22 utilizing any desired method.

Once the urethral element 60 is positioned on the elongated element 22, the inner insertion element 40 is then moved in the direction of the urethral element 60 while the outer insertion element 20 is held in place or moved away from the urethral element 60. Upon contacting the inner insertion element 40, the flange 64 folds into a U-shape, such as shown in FIG. 2A. Due to the friction between the surface of the flexible flange 64 and the inner surface of the inner insertion element 40, the flange 64 remains in its folded state. The inner insertion element 40 containing the folded flange 64 is further moved until the second body portion 46 is placed in contact with the cup-shaped end 65 of the urethral element. At this point, the intraurethral device 10 is assembled and ready for use.

Referring to FIGS. 2A–2D, one method for inserting the urethral element 60 of the intraurethral device 10 shown in FIG. 1 into a urethra is illustrated. In particular, as shown in FIG. 2A, a user or medical professional grasps the intraurethral device in an outwardly extended position and aligns the roll-out nipple 80 and urethral element 60 with a urethra opening. Once properly positioned, the outer insertion element 20 is moved toward the urethra, as indicated by the directional arrow of FIG. 2B. In some instances, it may be desired to simultaneously hold the inner insertion element 40 in place while the outer insertion element 20 is moved toward the urethra. The downward motion of the outer insertion element 20 causes the elongated element 22 and the urethral element 60 to be inserted into the urethra. In addition, as shown in FIGS. 2B and 5A–5B, the downward motion of the outer insertion element 20 causes the roll-out nipple 80 to unravel, such that the urethral element 60 does not generally come into contact with a non-sterile surface, and thus, does not drag substantial amounts of bacteria, fungi, or other pathogenic microorganisms into the urethra, prior to and/or during insertion.

In one embodiment, as shown in FIG. 3A, the outer body portion 26 contains two flanges 28. Thus, as the outer insertion element 20 is moved towards the urethra, the flanges 28 come into contact with the urethra wall, thereby inhibiting any further downward movement of the outer insertion element 20. In this manner, over-insertion of the urethral plug can be substantially prevented.

Once the urethral element 60 is positioned within the urethra, the inner insertion element 40 is then moved upward, as indicated by the directional arrow shown in FIG. 2C. In some instances, it may also be desired to simultaneously hold the outer insertion element 20 in place while moving the inner insertion element 40 away from the urethra. The upward motion of the inner insertion element 40 causes the urethral plug 60 to be released from the elongated element 22, thereby unrolling the flange 64 of the urethral element 60 from its U-shaped position into a flat position, such as shown in FIG. 2C. Because the unrolled flange 64 has a width greater than the width of the urethra opening, it can inhibit over-insertion of the urethral element 60 therein.

After inserting the urethral element 60, the insertion elements 20 and 40 can then be completely removed. For example, as depicted in FIG. 2D, a user can withdraw the elongated element 22 by pulling the insertion element 20 in an outwardly direction, as indicated by the directional arrow depicted in FIG. 2D. If desired, the outside of the urethral element 60 can also be also coated with a lubricant, such as VASELINE or K-Y JELLY, prior to insertion into the urethra in order to protect sensitive urethral tissue.

The urethral element 60, which is now positioned within the urethra, can deliver one or more chemical compounds for treating various diseases or infections, or can detect the presence of such diseases or chemicals.

In general, the urethral element 60 can be removed in a variety of ways. In most instances, the urethral element 60 can be removed without the aid of a medical professional. In particular, removal can normally be accomplished manually or by voluntary urinary exertion. Moreover, although not necessary, a variety of other mechanisms can also be utilized to facilitate the removal of the urethral element 60. For instance, in some embodiments, the urethral element 60 can include a removal device (not shown), such as a string, filament, cord, tether, and the like, to facilitate manual removal of the urethral element 60. A removal device can generally allow the patient to facilitate manual plug removal as desired, by manually exerting pressure on the device. Additionally, should expulsion not occur when the urethral element 60 is released from its intraurethral location, a removal device can also allow the patient to completely remove the urethral element 60. It should be understood that a removal device may be secured to the urethral element 60 by any suitable method known in the art, as long as adequate strength is present to facilitate manual removal of the urethral element 60 by applying a force to the removal device. For example, in one embodiment, the removal device may be molded as a unitary structure with the urethral element 60.

These and other modifications and variations of the present invention may be practiced by those of ordinary skill in the art, without departing from the spirit and scope of the present invention, which is set forth in the appended claims. In addition, it should be understood that aspects of the various embodiments may be interchanged both in whole or in part. Furthermore, those of ordinary skill in the art will appreciate that the foregoing description is by way of example only, and is not intended to limit the invention so further described in such appended claims.

What is claimed is:

1. A method of treating a disease or disorder, said method comprising:

a) providing an intraurethral device that comprises a urethral element having a distal end, a proximal end, and a connecting section therebetween, the distal end defining a first outer cross-sectional dimension and a height and the connecting section defining a second outer cross-sectional dimension, wherein the outer cross-sectional dimension of the distal end is greater than the outer cross-sectional dimension of the connecting section, said distal end of said urethral element being adapted to be inserted into a urethra, said distal end containing a chemical compound capable of treating or detecting the presence or absence of a disorder or disease, wherein the shape of said distal end forms a recess that is closed at the interior terminus of the recess, the recess defining a height that is less than the height of the distal end such that said recess is contained within the distal end and does not extend into the connecting section of the urethral element;

b) inserting said urethral element into the urethra so that said chemical compound is not substantially contaminated prior to insertion of said urethral element in the urethra; and c) allowing said chemical compound to be released from said urethral element into the urethra.

2. A method as defined in claim 1, wherein the shape of said recess defines a generally concave surface.

3. A method as defined in claim 1, wherein said intraurethral device further comprises:

a first insertion element having an inner surface and an outer surface, wherein at least a portion of said first insertion element is in operative communication with said urethral element; and a second insertion element having an inner surface and an outer surface, said second insertion element defining a channel through which said proximal end of said urethral element is capable of being inserted, wherein said inner surface of said second insertion element is placed adjacent to said outer surface of said first insertion element such that said second insertion element is in operative communication with said first insertion element.

4. A method as defined in claim 1, wherein said chemical compound is capable of treating bladder infections.

5. A method as defined in claim 1, wherein said chemical compound is selected from the group consisting of antibiotics, hormones, astringents, anti-inflammatory agents, medications, doxorubicin, *mycobacterium*, sodium pentosan-polysulfate, oxychorosens, natruim chromogulcate, steroids, quinolones, and combinations thereof.

6. A method as defined in claim 1, wherein said chemical compound is disposed on a surface of said urethral element.

7. A method as defined in claim 6, wherein said chemical compound is disposed on the surface of the recess of the distal end of the urethral element.

8. A method as defined in claim 1, wherein the outer cross-sectional dimension of the distal end of the urethral element is such that said urethral element forms a seal with the urethra when inserted therein.

\* \* \* \* \*